United States Patent
Amagai et al.

(10) Patent No.: US 7,309,794 B1
(45) Date of Patent: *Dec. 18, 2007

(54) METHOD OF STORING EPISULFIDE COMPOUND

(75) Inventors: Akikazu Amagai, Tokyo (JP); Yuichi Yoshimura, Mie (JP); Motoharu Takeuchi, Tokyo (JP); Atsuki Niimi, Tokyo (JP); Hiroshi Horikoshi, Chiba (JP); Masanori Shimuta, Mie (JP); Nobuyuki Uemura, Osaka (JP)

(73) Assignee: Mitsubishi Gas Chemical Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/415,906

(22) PCT Filed: Nov. 7, 2000

(86) PCT No.: PCT/JP00/07807

§ 371 (c)(1),
(2), (4) Date: May 5, 2003

(87) PCT Pub. No.: WO02/38558

PCT Pub. Date: May 16, 2002

(51) Int. Cl.
*C07D 331/02* (2006.01)
(52) U.S. Cl. .......................................................... 549/90
(58) Field of Classification Search ................... 549/90
See application file for complete search history.

(56) References Cited

U.S. PATENT DOCUMENTS 6,225,439 B1 * 5/2001 Amagai et al. ............. 528/380

FOREIGN PATENT DOCUMENTS

| EP | 0 761 665 | 3/1997 |
|---|---|---|
| EP | 0 785 194 | 7/1997 |
| JP | 2000-186086 | 7/2000 |
| JP | 2000-186087 | 7/2000 |
| JP | 2000-327677 | 11/2000 |

\* cited by examiner

*Primary Examiner*—Bernard Dentz
(74) *Attorney, Agent, or Firm*—Antonelli, Terry, Stout & Kraus, LLP.

(57) ABSTRACT

Episulfide compounds useful as starting materials of optical materials are stably stored for a long period of time at a temperature ranging from their solidifying points to 20° C., preventing the production or precipitation of polymers and the yellowing.

15 Claims, No Drawings

METHOD OF STORING EPISULFIDE COMPOUND

TECHNICAL FIELD

The present invention relates to a method for storing episulfide compounds for producing optical materials such as plastic lens, prisms, optical fibers, substrates of information recording media, and filters, in particular, plastic lens for spectacles.

BACKGROUND ARTS

Plastic materials have been recently increasingly used as various optical materials, in particular, as lens for spectacles, because of light weight, high toughness and good dyeing ability. The optical materials, especially lens for spectacles, are required to exhibit good properties such as low specific gravity, high transparency and low yellowness as well as optical properties such as high refractive index and large Abbe number. The high refractive index reduces the thickness of lens and the high Abbe number reduces the chromatic aberration of lens. The present inventors found novel episulfide compounds capable of providing optical materials having a small thickness and exhibiting a low chromatic aberration attributable to its refractive index of 1.7 or higher and Abbe number of 35 or larger, and have filed patent applications (Japanese Patent Application Laid-Open Nos. 9-71580, 9-110979 and 9-255781). However, the episulfide compounds cause precipitation or formation of polymers and yellowing within several days depending on storage conditions, especially, cause severe precipitation when solidified. The polymerization of such episulfide compounds results in optical materials having deteriorated quality due to cloudiness and yellowing. Therefore, to produce optical materials stably from episulfide compounds, it has been demanded to develop a method for stably storing the episulfide compounds for a long period of time.

DISCLOSURE OF THE INVENTION

An object of the present invention is to overcome the above conventional problems and provide a method for stably storing episulfide compounds having in one molecule, at least one structural unit represented by the following formula (1):

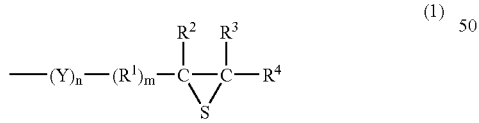

(1)

wherein $R^1$ is a $C_1$-$C_{10}$ hydrocarbon group; $R^2$, $R^3$ and $R^4$ are independently a $C_1$-$C_{10}$ hydrocarbon group or hydrogen; Y is O, S, Se or Te; n is 0 or 1; and m is 0 or 1, without precipitation or formation of polymers and yellowing.

The present inventors have found that the episulfide compound having at least one epithio structural unit represented by the formula (1) in one molecule is prevented from causing precipitation or formation of polymers and yellowing by controlling the storage temperature. The present invention has been accomplished on the basis of this finding.

Thus, the present invention provides a method for storing an episulfide compound having at least one epithio structural unit represented by the formula (1), which comprises a step of storing the episulfide compound at temperatures from its solidifying point to 20° C.

PREFERRED EMBODIMENT TO CARRY OUT THE INVENTION

The episulfide compound having one or more epithio structural units represented by the formula (1) according to the present invention may include all organic compounds satisfying the above requirements. Of these organic compounds, preferred are ones having two or more epithio structural units represented by the formula (1). Examples of the episulfide compounds having one or more epithio structural units represented by the formula (1) are as follows:

(A) organic compounds having epithio group;

(B) organic compounds having epithioalkyloxy group;

(C) organic compounds having epithioalkylthio group;

(D) organic compounds having epithioalkylseleno group; and (E) organic compounds having epithioalkyltelluro group.

The organic compounds (A), (B), (C), (D) and (E) have a main backbone structure derived from chain compound, branched compound, alicyclic compound, aromatic compound or heterocyclic compound containing nitrogen, oxygen, sulfur, selenium or tellurium, and may have epithio, epithioalkyloxy, epithioalkylthio, epithioalkylseleno and epithioalkyltelluro groups in one molecule at the same time. Also, these organic compounds may further have various linkages such as sulfide, selenide, telluride, ether, sulfone, ketone, ester, amide and urethane linkages in the molecule.

(A) The organic compounds having one or more epithio groups are preferably obtained by replacing one or more epoxy groups (except glycidyl) of epoxy compounds with one or more epithio groups.

Examples thereof are mentioned below.

Organic Compounds Having Aliphatic Chain Backbone 1,1-bis(epithioethyl)methane, 1-(epithioethyl)-1-(β-epithiopropyl)methane, 1,1-bis(β-epithiopropyl)methane, 1-(epithioethyl)-1-(β-epithiopropyl)ethane, 1,2-bis(β-epithiopropyl)ethane, 1-(epithioethyl)-3-(β-epithiopropyl)butane, 1,3-bis(β-epithiopropyl)propane, 1-(epithioethyl)-4-(β-epithiopropyl)pentane, 1,4-bis(β-epithiopropyl)butane, 1-(epithioethyl)-5-(β-epithiopropyl)hexane, 1-(epithioethyl)-2-(γ-epithiobutylthio)ethane, 1-(epithioethyl)-2-[2-(γ-epithiobutylthio)ethylthio]ethane, tetrakis(β-ethylpropyl)methane, 1,1,1-tris(β-epithiopropyl)propane, 1,3-bis(β-epithiopropyl)-1-(β-epithiopropyl)-2-thiapropane, and 1,5-bis(β-epithiopropyl)-2,4-bis(β-epithiopropyl)-3-thiapentane.

Compounds Having Alicyclic Backbone compounds having one alicyclic structure such as 1,3- or 1,4-bis(epithioethyl)cyclohexane, 1,3- or 1,4-bis(β-epithiopropyl)cyclohexane, 2,5-bis(epithioethyl)-1,4-dithiane, 2,5-bis(β-epithiopropyl)-1,4-dithiane, 4-epithioethyl-1,2-cyclohexene sulfide and 4-epoxy-1,2-cyclohexene sulfide, and compounds having two alicyclic structures such as 2,2-bis[4-(epithioethyl)cyclohexyl]propane, 2,2-bis[4-(β-epithiopropyl)cyclohexyl]propane, bis[4-(epithioethyl)cyclohexyl]methane, bis[4-(β-epithiopropyl)cyclohexyl]methane, bis[4-(β-epithiopropyl)cyclohexyl]sulfide, and bis[4-(epithioethyl)cyclohexyl]sulfide.

Compounds Having Aromatic Backbone compounds having one aromatic structure such as 1,3- or 1,4-bis(epithioethyl)benzene and 1,3- or 1,4-bis(β-epithiopropyl)benzene, and compounds having two aromatic structures such as bis[4-(epithioethyl)phenyl]methane, bis[4-(β-epithiopropyl)phenyl]methane, 2,2-bis[4-(epithioethyl)phenyl]propane, 2,2-bis[4-(β-epithiopropyl)phenyl]propane, bis[4-(epithioethyl)phenyl]sulfide, bis[4-(β-epithiopropyl)phenyl]sulfide, bis[4-(epithioethyl)phenyl]sulfone, bis[4-(β-epithiopropyl)phenyl]sulfone, 4,4'-bis(epithioethyl)biphenyl, and 4,4'-bis(β-epithiopropyl)biphenyl.

Also included are compounds obtained by replacing at least one hydrogen atom of the epithio group of the above-described compounds with a methyl group.

(B) The organic compound having one or more epithioalkyloxy groups are preferably obtained by replacing one or more glycidyl groups of epoxy compounds derived from epihalohydrin with epithioalkyloxy groups. Examples of the epoxy compounds include phenolic epoxy compounds produced by condensing epihalohydrin with a polyhydric phenol compound such as hydroquinone, catechol, resorcin, bisphenol A, bisphenol F, bisphenol sulfone, bisphenol ether, bisphenol sulfide, halogenated bisphenol A and novolak resins; alcoholic epoxy compounds produced by condensing epihalohydrin with a polyhydric alcohol compound such as ethylene glycol, diethylene glycol, triethylene glycol, polyethylene glycol, propylene glycol, dipropylene glycol, polypropylene glycol, 1,3-propanediol, 1,4-butanediol, 1,6-hexanediol, neopentyl glycol, glycerin, trimethylolpropane trimethacrylate, pentaerythritol, 1,3- or 1,4-cyclohexanediol, 1,3- or 1,4-cyclohexanedimethanol, hydrogenated bisphenol A, bisphenol A-ethylene oxide adduct and bisphenol A-propylene oxide adduct; glycidyl ester epoxy compounds produced by condensing epihalohydrin with a polycarboxylic acid such as adipic acid, sebacic acid, dodecanedicarboxylic acid, dimer acid, phthalic acid, isophthalic acid, terephthalic acid, tetrahydrophthalic acid, methyltetrahydrophthalic acid, hexahydrophthalic acid, hexahydroisophthalic acid, hexahydroterephthalic acid, HET acid, nagic acid, maleic acid, succinic acid, fumaric acid, trimellitic acid, benzenetetracarboxylic acid, benzophenonetetracarboxylic acid, naphthalenedicarboxylic acid and diphenyldicarboxylic acid; amine epoxy compounds produced by condensing epihalohydrin with a primary diamine such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis(3-aminopropyl)ether, 1,2-bis(3-aminopropoxy)ethane, 1,3-bis(3-aminopropoxy)-2,2'-dimethylpropane, 1,2-, 1,3- or 1,4-bisaminocyclohexane, 1,3- or 1,4-bisaminomethylcyclohexane, 1,3- or 1,4-bisaminoethylcyclohexane, 1,3- or 1,4-bisaminopropylcyclohexane, hydrogenated 4,4'-diaminodiphenylmethane, isophoronedimaine, 1,4-bisaminopropylpiperazine, m- or p-phenylenediamine, 2,4- or 2,6-tolylenediamine, m- or p-xylylenediamine, 1,5- or 2,6-naphthalenediamine, 4,4'-diaminodiphenylmethane, 4,4'-diaminodiphenyl ether and 2,2-(4,4'-diaminodiphenyl)propane, or a secondary diamine such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-diemthyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5- or 2,6-dimethylpiperazine, homopiperazine, 1,1-di(4-piperidinyl)methane, 1,2-di(4-piperidinyl)ethane, 1,3-di(4-piperidinyl)propane and 1,4-di(4-piperidinyl)butane; and urethane epoxy compounds produced by reacting the above polyhydric alcohol or phenol compound with diisocyanate, glycidol, etc. Examples of the organic compounds (B) are mentioned below. Organic compounds having aliphatic chain backbone bis(β-epithiopropyl)ether, bis(β-epithiopropyloxy)methane, 1,2-bis(β-epithiopropyloxy)ethane, 1,3-bis(β-epithiopropyloxy)propane, 1,2-bis(β-epithiopropyloxy)propane, 1-(β-epithiopropyloxy)-2-(β-epithiopropyloxymethyl) propane, 1,4-bis(β-epithiopropyloxy)butane, 1,3-bis(β-epithiopropyloxy)butane, 1-(β-epithiopropyloxy)-3-(β-epithiopropyloxymethyl)butane, 1,5-bis(β-epithiopropyloxy)pentane, 1-(β-epithiopropyloxy)-4-(β-epithiopropyloxymethyl)pentane, 1,6-bis(β-epithiopropyloxy)hexane, 1-(β-epithiopropyloxy)-5-(β-epithiopropyloxymethyl)hexane, 1-(β-epithiopropyloxy)-2-[(2-β-epithiopropyloxyethyl)oxy]ethane, 1-(β-epithiopropyloxy)-2-[[2-(2-β-epithiopropyloxyethyl)oxyethyl]oxy]ethane, tetrakis(β-epithiopropyloxymethyl)methane, 1,1,1-tris(β-epithiopropyloxymethyl)propane, 1,5-bis(β-epithiopropyloxy)-2-(β-epithiopropyloxymethyl)-3-thiapentane, 1,5-bis(β-epithiopropyloxy)-2,4-bis(β-epithiopropyloxymethyl)-3-thiapentane, 1-(β-epithiopropyloxy)-2,2-bis(β-epithiopropyloxymethyl)-4-thiahexane, 1,5,6-tris(β-epithiopropyloxy)-4-(β-epithiopropyloxymethyl)-3-thiahexane, 1,8-bis(β-epithiopropyloxy)-4-(β-epithiopropyloxymethyl)-3,6-dithiaoctane, 1,8-bis(β-epithiopropyloxy)-4,5-bis(β-epithiopropyloxymethyl)-3,6-dithiaoctane, 1,8-bis(β-epithiopropyloxy)-4,4-bis(β-epithiopropyloxymethyl)-3,6-dithiaoctane, 1,8-bis(β-epithiopropyloxy)-2,4,5-tris(β-epithiopropyloxymethyl)-3,6-dithiaoctane, 1,8-bis(β-epithiopropyloxy)-2,5-bis(β-epithiopropyloxymethyl)-3,6-dithiaoctane, 1,9-bis(β-epithiopropyloxy)-5-(β-epithiopropyloxymethyl)-5-[(2-β-epithiopropyloxyethyl)oxymethyl]-3,7-dithianonane, 1,10-bis(β-epithiopropyloxy)-5,6-bis[(2-β-epithiopropyloxyethyl)oxy]-3,6,9-trithiadecane, 1,11-bis(β-epithiopropyloxy)-4,8-bis(β-epithiopropyloxymethyl)-3,6,9-trithiadecane, 1,11-bis(β-epithiopropyloxy)-5,7-bis(β-epithiopropyloxymethyl)-3,6,9-trithiaundecane, 1,11-bis(β-epithiopropyloxy)-5,7-[(2-β-epithiopropyloxyethyl)oxymethyl]-3,6,9-trithiaundecane, and 1,11-bis(β-epithiopropyloxy)-4,7-bis(β-epithiopropyloxymethyl)-3,6,9-trithiaundecane.

Compounds Having Alicyclic Backbone 1,3- or 1,4-bis(β-epithiopropyloxy)cyclohexane, 1,3- or 1,4-bis(β-epithiopropyloxymethyl)cyclohexane, bis[4-(β-epithiopropyloxy)cyclohexyl]methane, 2,2-bis[4-(β-epithiopropyloxy)cyclohexyl]propane, bis[4-(β-epithiopropyloxy)cyclohexyl]sulfide, 2,5-bis(β-epithiopropyloxymethyl)-1,4-dithiane, and 2,5-bis(β-epithiopropyloxyethyloxymethyl)-1,4-dithiane.

Compounds Having Aromatic Backbone compounds having one aromatic structure such as 1,3- or 1,4-bis(β-epithiopropyloxy)benzene and 1,3- or 1,4-bis(β-epithiopropyloxymethyl)benzene, and compounds having two aromatic structures such as bis[4-(β-epithiopropylthio)

phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4'-bis(β-epithiopropylthio)biphenyl.

Also included are compounds obtained by replacing at least one hydrogen atom of the epithio group of the above compounds with a methyl group.

(C) The organic compounds having one or more epithioalkylthio groups are preferably obtained by replacing one or more epoxyalkylthio groups (specifically, β-epoxypropylthio groups) of epoxy compounds derived from a mercapto compound and epihalohydrin, with epithioalkylthio groups. Examples thereof are mentioned below.

Organic Compounds Having Aliphatic Chain Backbone
bis(β-epithiopropyl)sulfide, bis(β-epithiopropyl)disulfide, bis(β-epithiopropyl)trisulfide, bis(β-epithiopropylthio)methane, bis(β-epithiopropyldithio)methane, bis(β-epithiopropyldithio)ethane, bis(β-epithiopropyldithioethyl)sulfide, bis(β-epithiopropyldithioethyl)disulfide, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-(2-β-epithiopropylthioethyl)thio]ethane, 1-(β-epithiopropylthio)-2-[[(2-(2-β-epithiopropylthioethyl)thioethyl]thio]ethane, tetrakis(β-epithiopropylthiomethyl)methane, tetrakis(β-epithiopropyldithiomethyl)methane, 1,1,1-tris(β-epithiopropylthiomethyl)propane, 1,2,3-tris(β-epithiopropyldithio)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1,6-bis(β-epithiopropyldithiomethyl)-2-(β-epithiopropyldithioethylthio)-4-thiahexane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, and 1,11-bis(β-epithiopropylthio)-4,7-bis(β-epithiopropylthiomethyl)-3,6,9-trithiaundecane.

Chain Compounds Having Ester Group and Epithioalkylthio Group
tetra[2-(β-epithiopropylthio)acetylmethyl]methane, 1,1,1-tri[2-(β-epithiopropylthio)acetylmethyl]propane, tetra[2-(β-epithiopropylthiomethyl)acetylmethyl]methane, and 1,1,1-tri[2-(β-epithiopropylthiomethyl)acetylmethyl]propane.

Compounds Having Alicyclic Backbone
compounds having one alicyclic structure such as 1,3- or 1,4-bis(β-epithiopropylthio)cyclohexane, 1,3- or 1,4-bis(β-epithiopropylthiomethyl)cyclohexane, 2,5-bis(β-epithiopropylthiomethyl)-1,4-dithiane, 2,5-bis(β-epithiopropyldithiomethyl)-1,4-dithiane and 2,5-bis(β-epithiopropylthioethylthiomethyl)-1,4-dithiane; and compounds having two alicyclic structures such as bis[4-(β-epithiopropylthio)cyclohexyl]methane, 2,2-bis[4-(β-epithiopropylthio)cyclohexyl]propane and bis[4-(β-epithiopropylthio)cyclohexyl]sulfide.

Compounds Having Aromatic Backbone
compounds having one aromatic structure such as 1,3- or 1,4-bis(β-epithiopropylthio)benzene, 1,3- or 1,4-bis(β-epithiopropylthiomethyl)benzene and 1,3- or 1,4-bis(β-epithiopropyldithiomethyl)benzene, and compounds having two aromatic structures such as bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4'-bis(β-epithiopropylthio)biphenyl.

Also included are compounds obtained by replacing at least one hydrogen atom of β-epithiopropyl group of the above compounds with a methyl group.

(D) The organic compounds having epithioalkylseleno group are preferably obtained by replacing one or more epoxyalkylseleno groups (specifically, β-epoxypropylseleno groups) of epoxy compound derived from epihalohydrin and metallic selenium or a selenium compound such as alkali metal selenide, alkali metal selenol, alkyl(aryl)selenol and hydrogen selenide, with epithioalkylseleno group. Examples thereof are mentioned below.

Organic Compounds Having Aliphatic Chain Backbone
bis(β-epithiopropyl)selenide, bis(β-epithiopropyl)diselenide, bis(β-epithiopropyl)triselenide, bis(β-epithiopropylseleno)methane, 1,2-bis(β-epithiopropylseleno)ethane, 1,3-bis(β-epithiopropylseleno)propane, 1,2-bis(β-epithiopropylseleno)propane, 1-(β-epithiopropylseleno)-2-(β-epithiopropylselenomethyl)propane, 1,4-bis(β-epithiopropylseleno)butane, 1,3-bis(β-epithiopropylseleno)butane, 1-(β-epithiopropylseleno)-3-(β-epithiopropylselenomethyl)butane, 1,5-bis(β-epithiopropylseleno)pentane, 1-(β-epithiopropylseleno)-4-(β-epithiopropylselenomethyl)pentane, 1,6-bis(β-epithiopropylseleno)hexane, 1-(β-epithiopropylseleno)-5-(β-epithiopropylselenomethyl)hexane, 1-(β-epithiopropylseleno)-2-[(2-β-epithiopropylselenoethyl)thio]ethane, 1-(β-epithiopropylseleno)-2-[[2-(2-β-epithiopropylselenoethyl)selenoethyl]thio]ethane, tetrakis(β-epithiopropylselenomethyl)methane, 1,1,1-tris(β-epithiopropylselenomethyl)propane, 1,5-bis(β-epithiopropylseleno)-2-(β-epithiopropylselenomethyl)-3-thiapentane, 1,5-bis(β-epithiopropylseleno)-2,4-bis(β-epithiopropylselenomethyl)-3-thiapentane, 1-(β-epithiopropylseleno)-2,2-bis(β-epithiopropylselenomethyl)-4-thiahexane, 1,5,6-tris(β-epithiopropylseleno)-4-(β-epithiopropylselenomethyl)-3-thiahexane, 1,8-bis(β-epithiopropylseleno)-4-(β-epithiopropylselenomethyl)-3,6-dithiaoctane, 1,8-bis(β-epithiopropylseleno)-4,5-bis(β-epithiopropylselenomethyl)-3,6-dithiaoctane, 1,8-bis(β-epithiopropylseleno)-4,4-bis(β-epithiopropylselenomethyl)-3,6-dithiaoctane, 1,8-bis(β- epithiopropylseleno)-2,4,5-tris(β-epithiopropylselenomethyl)-3,6-dithiaoctane, 1,8-bis(β-epithiopropylseleno)-2,5-bis(β-epithiopropylselenomethyl)-3,6-dithiaoctane, 1,9-bis(β-epithiopropylseleno)-5-(β-epithiopropylselenomethyl)-5-[(2-β-epithiopropylselenoethyl)selenomethyl]-3,7-dithianonane, 1,10-bis(β-epithiopropylseleno)-5,6-bis[(2-β-epithiopropylselenoethyl)thio]-3,6,9-trithiadecane, 1,11-bis(β-epithiopropylseleno)-4,8-bis(β-epithiopropylselenomethyl)-3,6,9-trithiaundecane, 1,11-bis(β-epithiopropylseleno)-5,7-bis(β-epithiopropylselenomethyl)-3,6,9-trithiaundecane, 1,11-bis(β-epithiopropylseleno)-5,7-[(2-β-epithiopropylselenoethyl)selenomethyl]-3,6,9-trithiaundecane, 1,11-bis(β-epithiopropylseleno)-4,7-bis(β-epithiopropylselenomethyl)-3,6,9-trithiaundecane, tetra[2-(β-epithiopropylseleno)acetylmethyl]methane, 1,1,1-tri[2-(β-epithiopropylseleno)acetylmethyl]propane, tetra[2-(β-epithiopropylselenomethyl)acetylmethyl]methane, 1,1,1-tri[2-(β-epithiopropylselenomethyl)acetylmethyl]propane, bis(5,6-epithio-3-selenohexyl)selenide, 2,3-bis(6,7-thioepoxy-1-selena-4-selenoheptyl)-1-(3,4-thioepoxy-1-selenobutyl)propane, 1,1,3,3-tetrakis(4,5-thioepoxy-2-selenopentyl)-2-selenapropane, bis(4,5-thioepoxy-2-selenopentyl)-3,6,9-triselenaundecane-1,11-bis(3,4-thioepoxy-1-selenobutyl), 1,4-bis(3,4-thioepoxy-1-selenobutyl)-2,3-bis(6,7-thioepoxy-1-selena-4-selenoheptyl)butane, tris(4,5-thioepoxy-2-selenopentyl)-3-selena-6-thiaoctane-1,8-bis(3,4-thioepoxy-1-selenobutyl), bis(5,6-epithio-3-selenohexyl)telluride, 2,3-bis(6,7-thioepoxy-1-tellura-4-selenoheptyl)-1-(3,4-thioepoxy-1-selenobutyl)propane, 1,1,3,3-tetrakis(4,5-thioepoxy-2-selenopentyl)-2-tellurapropane, bis(4,5-thioepoxy-2-selenopentyl)-3,6,9-tritelluraundecane-1,11-bis(3,4-thioepoxy-1-selenobutyl), 1,4-bis(3,4-thioepoxy-1-selenobutyl)-2,3-bis(6,7-thioepoxy-1-tellura-4-selenoheptyl)butane, and tris(4,5-thioepoxy-2-selenopentyl)-3-tellura-6-thiaoctane-1,8-bis(3,4-thioepoxy-1-selenobutyl).

Compounds Having Alicyclic Backbone 1,3- or 1,4-bis(β-epithiopropylseleno)cyclohexane, 1,3- or 1,4-bis(β-epithiopropylselenomethyl)cyclohexane, bis[4-(β-epithiopropylseleno)cyclohexyl]methane, 2,2-bis[4-(β-epithiopropylseleno)cyclohexyl]propane, bis[4-(β-epithiopropylseleno)cyclohexyl]sulfide, 2,5-bis(β-epithiopropylselenomethyl)-1,4-dithiane, 2,5-bis(β-epithiopropylselenoethylthiomethyl)-1,4-dithiane, 2,3-, 2,5- or 2,6-bis(3,4-epithio-1-selenobutyl)-1,4-diselenane, 2,3-, 2,5- or 2,6-bis(4,5-epithio-2-selenopentyl)-1,4-diselenane, 2,4-, 2,5- or 5,6-bis(3,4-epithio-1-selenobutyl)-1,3-diselenane, 2,4-, 2,5- or 5,6-bis(4,5-epithio-2-selenopentyl)-1,3-diselenane, 2,3-, 2,5-, 2,6- or 3,5-bis(3,4-epithio-1-selenobutyl)-1-thia-4-selenane, 2,3-, 2,5-, 2,6- or 3,5-bis(4,5-epithio-2-selenopentyl)-1-thia-4-selenane, 2,4- or 4,5-bis(3,4-epithio-1-selenobutyl)-1,3-diselenolane, 2,4- or 4,5-bis(4,5-epithio-2-selenopentyl)-1,3-diselenolane, 2,4-, 2,5- or 4,5-bis(3,4-epithio-1-selenobutyl)-1-thia-3-selenolane, 2,4-, 2,5- or 4,5-bis(4,5-epithio-2-selenopentyl)-1-thia-3-selenolane, 2,6-bis(4,5-epithio-2-selenopentyl)-1,3,5-triselenane, bis(3,4-epithio-1-selenobutyl)tricycloselenaoctane, bis(3,4-epithio-1-selenobutyl)dicycloselenanonane, 2,3-, 2,4-, 2,5- or 3,4-bis(3,4-epithio-1-selenobutyl)selenophane, 2,3-, 2,4-, 2,5- or 3,4-bis(4,5-epithio-2-selenopentyl)selenophane, 2-(4,5-thioepoxy-2-selenopentyl)-5-(3,4-thioepoxy-1-selenobutyl)-1-selenacyclohexane, 2,3-, 2,4-, 2,5-, 2,6-, 3,4-, 3,5- or 4,5-bis(3,4-thioepoxy-1-selenobutyl)-1-selenacyclohexane, 2,3-, 2,4-, 2,5-, 2,6-, 3,4-, 3,5- or 4,5-bis(4,5-thioepoxy-2-selenopentyl)-1-selenacyclohexane, 2,3-, 2,5- or 2,6-bis(3,4-epithio-1-selenobutyl)-1,4-ditellurane, 2,3-, 2,5- or 2,6-bis(4,5-epithio-2-selenopentyl)-1,4-ditellurane, 2,4-, 2,5- or 5,6-bis(3,4-epithio-1-selenobutyl)-1,3-ditellurane, 2,4-, 2,5- or 5,6-bis(4,5-epithio-2-selenopentyl)-1,3-ditellurane, 2,3-, 2,5-, 2,6- or 3,5-bis(3,4-epithio-1-selenobutyl)-1-thia-4-tellurane, 2,3-, 2,5-, 2,6- or 3,5-bis(4,5-epithio-2-selenopentyl)-1-thia-4-tellurane, 2,4- or 4,5-bis(3,4-epithio-1-selenobutyl)-1,3-ditellurolane, 2,4- or 4,5-bis(4,5-epithio-2-selenopentyl)-1,3-ditellurolane, 2,4-, 2,5- or 4,5-bis(3,4-epithio-1-selenobutyl)-1-thia-3-tellurolane, 2,4-, 2,5- or 4,5-bis(4,5-epithio-2-selenopentyl)-1-thia-3-tellurolane, 2,6-bis(4,5-epithio-2-selenopentyl)-1,3,5-tritellurane, bis(3,4-epithio-1-selenobutyl)tricycloturaoctane, bis(3,4-epithio-1-selenobutyl)dicycloturanonane, 2,3-, 2,4-, 2,5- or 3,4-bis(3,4-epithio-1-selenobutyl)tellurophane, 2,3-, 2,4-, 2,5- or 3,4-bis(4,5-epithio-2-selenopentyl)tellurophane, 2-(4,5-thioepoxy-2-selenopentyl)-5-(3,4-thioepoxy-1-selenobutyl)-1-telluracyclohexane, 2,3-, 2,4-, 2,5-, 2,6-, 3,4-, 3,5- or 4,5-bis(3,4-thioepoxy-1-selenobutyl)-1-telluracyclohexane, and 2,3-, 2,4-, 2,5-, 2,6-, 3,4-, 3,5- or 4,5-bis(4,5-thioepoxy-2-selenopentyl)-1-telluracyclohexane.

Compounds Having Aromatic Backbone 1,3- or 1,4-bis(β-epithiopropylseleno)benzene, 1,3- or 1,4-bis(β-epithiopropylselenomethyl)benzene, bis[4-(β-epithiopropylseleno)phenyl]methane, 2,2-bis[4-(β-epithiopropylseleno)phenyl]propane, bis[4-(β-epithiopropylseleno)phenyl]sulfide, bis[4-(β-epithiopropylseleno)phenyl]sulfone and 4,4'-bis(β-epithiopropylseleno)biphenyl.

Also included are compounds obtained by replacing at least one hydrogen atom of β-epithiopropyl group in the above compounds with methyl group.

(E) The organic compounds having epithioalkyltelluro group are preferably obtained by replacing at least one epoxyalkyltelluro group (specifically, β-epoxyalkyltelluro group) of epoxy compounds derived from epihalohydrin and metallic tellurium or a tellurium compound such as alkali metal telluride, alkali metal tellurol, alkyl(aryl)tellurol and hydrogen telluride, with epithioalkyltelluro group. Examples thereof are mentioned below.

Organic Compounds Having Aliphatic Chain Backbone bis(β-epithiopropyl)telluride, bis(β-epidithiopropyl)ditelluride, bis(β-epithiopropyl)tritelluride, bis(β-epithiopropylturo)methane, 1,2-bis(β-epithiopropyltelluro)ethane, 1,3-bis(β-epithiopropyltelluro)propane, 1,2-bis(β-epithiopropyltelluro)propane, 1-(β-epithiopropyltelluro)-2-(β-epithiopropyltelluromethyl)propane, 1,4-bis(β-epithiopropyltelluro)butane, 1,3-bis(β-epithiopropyltelluro)butane, 1-(β-epithiopropyltelluro)-3-(β-epithiopropyltelluromethyl)butane, 1,5-bis(β-epithiopropyltelluro)pentane, 1-(β-epithiopropyltelluro)-4-(β-epithiopropyltelluromethyl)pentane, 1,6-bis(β-epithiopropyltelluro)hexane, 1-(β-epithiopropyltelluro)-5-(β-epithiopropyltelluromethyl)hexane, 1-(β-epithiopropyltelluro)-2-[(2-β-epithiopropyltelluroethyl)thio]ethane, 1-(β-epithiopropyltelluro)-2-[[2-(2-β-epithiopropyltelluroethyl)telluroethyl]thio]ethane, tetrakis(β-epithiopropyltelluromethyl)methane, 1,1,1-tris(β-epithiopropyltelluromethyl)propane, 1,5-bis(β-epithiopropyltelluro)-2-(β-epithiopropyltelluromethyl)-3-thiapentane, 1,5-bis(β-epithiopropyltelluro)-2,4-bis(β- epithiopropyltelluromethyl)-3-thiapentane, 1-(β-epithiopropyltelluro)-2,2-bis(β-epithiopropyltelluromethyl)-4-thiahexane, 1,5,6-tris(β-epithiopropyltelluro)-4-(β-epithiopropyltelluromethyl)-3-thiahexane, 1,8-bis(β-epithiopropyltelluro)-4-(β-epithiopropyltelluromethyl)-3,6-dithiaoctane, 1,8-bis(β-epithiopropyltelluromethyl)-4,5-bis(β-epithiopropyltelluro)-3,6-dithiaoctane, 1,8-bis(β-epithiopropyltelluromethyl)-4,4-bis(β-epithiopropyltelluro)-3,6-dithiaoctane, 1,8-bis(β-epithiopropyltelluromethyl)-2,4,5-tris(β-epithiopropyltelluro)-3,6-dithiaoctane, 1,8-bis(β-epithiopropyltelluromethyl)-2,5-bis(β-epithiopropyltelluro)-3,6-dithiaoctane, 1,9-bis(β-epithiopropyltelluro)-5-(β-epithiopropyltelluromethyl)-5-[(2-β-epithiopropyltelluroethyl)selenomethyl]-3,7-dithianonane, 1,10-bis(β-epithiopropyltelluro)-5,6-bis[(2-β-epithiopropyltelluroethyl)thio]-3,6,9-trithiadecane, 1,11-bis(β-epithiopropyltelluro)-4,8-bis(β-epithiopropyltelluromethyl)-3,6,9-trithiaundecane, 1,11-bis(β-epithiopropyltelluro)-5,7-bis(β-epithiopropyltelluromethyl)-3,6,9-trithiaundecane, 1,11-bis(β-epithiopropyltelluro)-5,7-[(2-β-epithiopropyltelluroethyl)selenomethyl]-3,6,9-trithiaundecane, 1,11-bis(β-epithiopropyltelluro)-4,7-bis(β-epithiopropyltelluromethyl)-3,6,9-trithiaundecane, tetra[2-(β-epithiopropyltelluro)acetylmethyl]methane, 1,1,1-tri[2-(β-epithiopropyltelluro)acetylmethyl]propane, tetra[2-(β-epithiopropyltelluromethyl)acetylmethyl]methane, 1,1,1-tri[2-(β-epithiopropyltelluromethyl)acetylmethyl]propane, bis(5,6-epithio-3-tellurohexyl)selenide, 2,3-bis(6,7-thioepoxy-1-selena-4-telluroheptyl)-1-(3,4-thioepoxy-1-tellurobutyl)propane, 1,1,3,3-tetrakis(4,5-thioepoxy-2-telluropentyl)-2-selenapropane, bis(4,5-thioepoxy-2-telluropentyl)-3,6,9-triselenaundecane-1,11-bis(3,4-thioepoxy-1-tellurobutyl), 1,4-bis(3,4-thioepoxy-1-tellurobutyl)-2,3-bis(6,7-thioepoxy-1-selena-4-telluroheptyl)butane, tris(4,5-thioepoxy-2-telluropentyl)-3-selena-6-thiaoctane-1,8-bis(3,4-thioepoxy-1-tellurobutyl), bis(5,6-epithio-3-tellurohexyl)telluride, 2,3-bis(6,7-thioepoxy-1-tellura-4-telluroheptyl)-1-(3,4-thioepoxy-1-tellurobutyl)propane, 1,1,3,3-tetrakis(4,5-thioepoxy-2-telluropentyl)-2-tellurapropane, bis(4,5-thioepoxy-2-telluropentyl)-3,6,9-tritelluraundecane-1,11-bis(3,4-thioepoxy-1-tellurobutyl), 1,4-bis(3,4-thioepoxy-1-tellurobutyl)-2,3-bis(6,7-thioepoxy-1-tellura-4-telluroheptyl)butane, and tris(4,5-thioepoxy-2-telluropentyl)-3-tellura-6-thiaoctane-1,8-bis(3,4-thioepoxy-1-tellurobutyl).

Compounds Having Alicyclic Backbone 1,3- or 1,4-bis(β-epithiopropyltelluro)cyclohexane, 1,3- or 1,4-bis(β-epithiopropyltelluromethyl)cyclohexane, bis[4-(β-epithiopropyltelluro)cyclohexyl]methane, 2,2-bis[4-(β-epithiopropyltelluro)cyclohexyl]propane, bis[4-(β-epithiopropyltelluro)cyclohexyl]sulfide, 2,5-bis(β-epithiopropyltelluromethyl)-1,4-dithiane, 2,5-bis(β-epithiopropyltelluroethylthiomethyl)-1,4-dithiane, 2,3-, 2,5- or 2,6-bis(3,4-epithio-1-tellurobutyl)-1,4-diselenane, 2,3-, 2,5- or 2,6-bis(4,5-epithio-2-telluropentyl)-1,4-diselenane, 2,4-, 2,5- or 5,6-bis(3,4-epithio-1-tellurobutyl)-1,3-diselenane, 2,4-, 2,5- or 5,6-bis(4,5-epithio-2-telluropentyl)-1,3-diselenane, 2,3-, 2,5-, 2,6- or 3,5-bis(3,4-epithio-1-tellurobutyl)-1-thia-4-selenane, 2,3-, 2,5-, 2,6- or 3,5-bis(4,5-epithio-2-telluropentyl)-1-thia-4-selenane, 2,4- or 4,5-bis(3,4-epithio-1-tellurobutyl)-1,3-diselenolane, 2,4- or 4,5-bis(4,5-epithio-2-telluropentyl)-1,3-diselenolane, 2,4-, 2,5- or 4,5-bis(3,4-epithio-1-tellurobutyl)-1-thia-3-selenolane, 2,4-, 2,5- or 4,5-bis(4,5-epithio-2-telluropentyl)-1-thia-3-selenolane, 2,6-bis(4,5-epithio-2-telluropentyl)-1,3,5-triselenane, bis(3,4-epithio-1-tellurobutyl)tricycloselenaoctane, bis(3,4-epithio-1-tellurobutyl)dicycloselenanonane, 2,3-, 2,4-, 2,5- or 3,4-bis(3,4-epithio-1-tellurobutyl)selenophane, 2,3-, 2,4-, 2,5- or 3,4-bis(4,5-epithio-2-telluropentyl)selenophane, 2-(4,5-thioepoxy-2-telluropentyl)-5-(3,4-thioepoxy-1-tellurobutyl)-1-selenacyclohexane, 2,3-, 2,4-, 2,5-, 2,6-, 3,4-, 3,5- or 4,5-bis(3,4-thioepoxy-1-tellurobutyl)-1-selenacyclohexane, 2,3-, 2,4-, 2,5-, 2,6-, 3,4-, 3,5- or 4,5-bis(4,5-thioepoxy-2-telluropentyl)-1-selenacyclohexane, 2,3-, 2,5- or 2,6-bis(3,4-epithio-1-tellurobutyl)-1,4-ditellurane, 2,3-, 2,5- or 2,6-bis(4,5-epithio-2-telluropentyl)-1,4-ditellurane, 2,4-, 2,5- or 5,6-bis(3,4-epithio-1-tellurobutyl)-1,3-ditellurane, 2,4-, 2,5- or 5,6-bis(4,5-epithio-2-telluropentyl)-1-3-ditellurane, 2,3-, 2,5-, 2,6- or 3,5-bis(3,4-epithio-1-tellurobutyl)-1-thia-4-tellurane, 2,3-, 2,5-, 2,6- or 3,5-bis(4,5-epithio-2-telluropentyl)-1-thia-4-tellurane, 2,4- or 4,5-bis(3,4-epithio-1-tellurobutyl)-1,3-ditellurolane, 2,4- or 4,5-bis(4,5-epithio-2-telluropentyl)-1,3-ditellurolane, 2,4-, 2,5- or 4,5-bis(3,4-epithio-1-tellurobutyl)-1-thia-3-tellurolane, 2,4-, 2,5- or 4,5-bis(4,5-epithio-2-telluropentyl)-1-thia-3-tellurolane, 2,6-bis(4,5-epithio-2-telluropentyl)-1,3,5-tritellurane, bis(3,4-epithio-1-tellurobutyl)tricyclotelluraoctane, bis(3,4-epithio-1-tellurobutyl)dicyclotelluranonane, 2,3-, 2,4-, 2,5- or 3,4-bis(3,4-epithio-1-tellurobutyl)tellurophane, 2,3-, 2,4-, 2,5- or 3,4-bis(4,5-epithio-2-telluropentyl)tellurophane, 2-(4,5-thioepoxy-2-telluropentyl)-5-(3,4-thioepoxy-1-tellurobutyl)-1-telluracyclohexane, 2,3-, 2,4-, 2,5-, 2,6-, 3,4-, 3,5- or 4,5-bis(3,4-thioepoxy-1-tellurobutyl)-1-telluracyclohexane, and 2,3-, 2,4-, 2,5-, 2,6-, 3,4-, 3,5- or 4,5-bis(4,5-thioepoxy-2-telluropentyl)-1-telluracyclohexane.

Compounds Having Aromatic Backbone 1,3- or 1,4-bis(β-epithiopropyltelluro)benzene, 1,3- or 1,4-bis(β-epithiopropyltelluromethyl)benzene, bis[4-(β-epithiopropyltelluro)phenyl]methane, 2,2-bis[4-(β-epithiopropyltelluro)phenyl]propane, bis[4-(β-epithiopropyltelluro)phenyl]sulfide, bis[4-(β-epithiopropyltelluro)phenyl]sulfone and 4,4'-bis(β-epithiopropyltelluro)biphenyl.

Also included are compounds obtained by replacing at least one hydrogen atom of β-epithiopropyl group in the above compounds with methyl group.

The organic compounds (A) to (E) may also have an unsaturated group. Examples thereof include vinylphenyl thioglycidyl ether, vinylbenzyl thioglycidyl ether, thioglycidyl methacrylate, thioglycidyl acrylate and allyl thioglycidyl ether.

In addition, examples of the compounds having one epithio group include compounds such as ethylene sulfide, propylene sulfide and thioglycidol, thioglycidyl esters of monocarboxylic acids such as acetic acid, propionic acid and benzoic acid, and thiglycodyl ethers such as methyl thioglycidyl ether, ethyl thioglycidyl ether, propyl thioglycidyl ether and butyl thioglycidyl ether.

Among the above compounds, preferred are the epithioalkyloxy-containing organic compounds (B), the epithioalkylthio-containing organic compounds (C), the epithioalkylseleno-containing organic compounds (D) and the epithioalkytelluro-containing organic compounds (E), more preferred are the epithioalkylthio-containing organic compounds (C) and the epithioalkylseleno-containing organic compounds (D), and still more preferred are chain compounds, branched compounds, alicyclic compounds, aromatic compounds and heterocyclic compounds each having β-epithiopropylthio group or β-epithiopropylseleno group. Of these, most preferred are the compounds represented by the following formula (2):

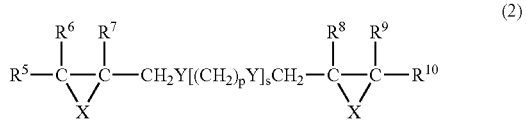

wherein $R^5$ to $R^{10}$ are independently a $C_1$-$C_{10}$ hydrocarbon group or hydrogen; X is S or O, the number of S being 50% or higher of a total number of S and O constituting three-membered rings; Y is O, S, Se or Te; p is an integer of 0 to 6; and s is an integer of 0 to 4.

The episulfide compound having in its molecule one or more epithio structural units represented by the formula (1) (hereinafter referred to as "episulfide compound") is produced by reacting a compound having an epoxy structural unit represented by the formula (3):

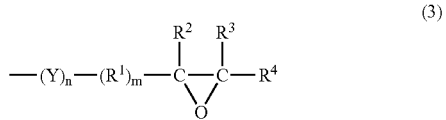

wherein $R^1$ is a $C_1$-$C_{10}$ hydrocarbon group; $R^2$, $R^3$ and $R^4$ are independently a $C_1$-$C_{10}$ hydrocarbon group or hydrogen; Y is O, S, Se or Te; n is 0 or 1; and m is 0 or 1, with a thia-introducing agent such as thiocyanates, thiourea, triphenylphosphine sulfide and 3-methylbenzothiazole-2-thione, preferably thiocyanates or thiourea.

Examples of the preferred thiocyanates used as the thia-introducing agent upon producing the episulfide compound from the epoxy compound having the structure represented by the general formula (3) are alkali metal salts or alkaline earth metal salts of thiocyanic acid, and ammonium thiocyanate, with potassium thiocyanate, sodium thiocyanate, barium thiocyanate and ammonium thiocyanate being more preferred. The thia-introducing agent such as thiocyanates and thiourea stoichiometrically reacts with an equimolar amount of the epoxy groups of the epoxy compound. When the purity of products, the reaction rate, the cost performance, etc. are important, the thia-introducing agent may be used above or below the stoichiometric amount. The thia-introducing agent is preferably used in an amount 1 to 5 times the stoichiometric amount, more preferably 1 to 2.5 times the stoichiometric amount. The reaction may be conducted in the presence or absence of solvent. A solvent, if used, that is capable of dissolving at least one of the thiocyanates, thiourea and the epoxy compounds is preferably used. Examples of the solvents include water; alcohols such as methanol and ethanol; ethers such as diethyl ether, tetrahydrofuran and dioxane; hydroxyethers such as methyl cellosolve, ethyl cellosolve and butyl cellosolve; aromatic hydrocarbons such as benzene, toluene and xylene; and halogenated hydrocarbons such as dichloroethane, chloroform and chlorobenzene. In some cases, effective results may be obtained by the use of the solvents in combination, for example, combinations of water with alcohols, and combinations of alcohols with ethers, hydroxyethers, halogenated hydrocarbons or aromatic hydrocarbons. Also, it is effective for good reaction results to add a polymerization inhibitor such as acids and acid anhydrides to the reaction solution. Examples of the acids and acid anhydrides include nitric acid, hydrochloric acid, sulfuric acid, fuming sulfuric acid, boric acid, arsenic acid, phosphoric acid, prussic acid, acetic acid, peracetic acid, thioacetic acid, oxalic acid, tartaric acid, propionic acid, butyric acid, succinic acid, maleic acid, benzoic acid, nitric anhydride, sulfuric anhydride, boron oxide, arsenic pentaoxide, phosphorus pentaoxide, chromic anhydride, acetic anhydride, propionic anhydride, butyric anhydride, succinic anhydride, maleic anhydride, benzoic anhydride, phthalic anhydride, silica gel, silica alumina and aluminum chloride. These acids and acid anhydrides may be used in combination of two or more. The polymerization inhibitor may be usually added in an amount of 0.001 to 10% by weight and preferably 0.01 to 5% by weight based on the total amount of the reaction solution. The reaction temperature is usually 0 to 100° C. and preferably 10 to 40° C. The reaction time may be selected so as to complete the reaction under the conditions mentioned above, and is usually 20 h or shorter. The reaction product may be washed with an aqueous acid solution to improve the stability of the obtained compound. Examples of acids to be contained in the aqueous acid solution include nitric acid, hydrochloric acid, sulfuric acid, boric acid, arsenic acid, phosphoric acid, prussic acid, acetic acid, peracetic acid, thioacetic acid, oxalic acid, tartaric acid, succinic acid and maleic acid. These acids may be used alone or in combination of two or more. The aqueous acid solution shows sufficient washing effect usually at a pH of 6 or lower, and preferably at a pH of 3 to 0.

Alternatively, the episulfide compound may also be effectively produced by dehydrohalogenating a halomercaptan compound having the structure represented by the formula (4):

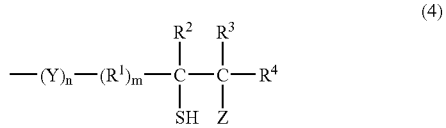

wherein $R^1$ is a $C_1$-$C_{10}$ hydrocarbon group; $R^2$, $R^3$ and $R^4$ are each independently a $C_1$-$C_{10}$ hydrocarbon group or hydrogen; Y is O, S, Se or Te; Z is halogen; n is 0 or 1; and m is 0 or 1.

It is known that the halomercaptan is easily synthesized, for example, by reacting an unsaturated compound with sulfur chlorides (e.g., F. Lautenschlaerger et al., "J. Org. Chem.", 34, 396 (1969)).

Purification of the episulfide compound by filtration is a very important procedure for obtaining an optical material having an improved quality. The episulfide compound is stored at a temperature of from its solidifying point to 20° C. prior to the filtration. When stored at a temperature less than its solidifying point, the episulfide compound may be crystallized to produce fine white precipitates attributable to its polymers, thereby rendering the subsequent filtration difficult. When stored over 20° C., the optical material obtained by polymerization becomes cloudy. The episulfide compound is filtered at a temperature ranging from its solidifying point to 20° C. using a filter having a pore diameter of about 0.05 to 10 μm (inclusive of the expression based on retained particle size) to remove impurities, polymers, etc. When the pore diameter is less than 0.05 μm, the filtration speed is lowered or the filtrate fails to flow therethrough, resulting in a substantial failure in filtration. When the pore diameter exceeds 10 μm, insoluble substances such as foreign materials and polymers are not sufficiently removed, resulting in a poor quality of the optical material obtained by polymerization due to residual foreign materials or cloudiness. The filter to be used for filtration is required to be resistant against the episulfide compound, namely, is required to cause no significant change in filter such as swelling and dissolution upon contacting the episulfide compound. If the filter is swelled upon filtration of the episulfide compound, the opening of the filter is compressed and contracted to make the filtration difficult. If the filter is dissolved, the dissolved matter is included into the episulfide compound to cause the cloudiness of the optical material obtained by polymerization. Examples of the filter materials resistant to the episulfide compound include glass fibers, carbon fibers, silicon fibers, metals such as titanium and zinc, alloys represented by stainless steel, polyolefins such as PTFE, PFA and polypropylene, polyesters such as polyethylene terephthalate, polyamides such as nylon 66, and ceramics. These materials are preferably applied to not only the filter, but also portions that come into contact with the episulfide compound, such as housing and gaskets.

In the method of storing the episulfide compound of the present invention, the storage temperature is important. In addition, the episulfide compound is more stably stored by controlling the oxygen concentration of storage atmosphere within an appropriate range, by adding a stabilizer, or by selecting an appropriate material for storage container. The storage temperature is in the range from its solidifying point to 20° C. and preferably from its solidifying point to 10° C. Storage temperatures less than the solidifying point cause solidification of the episulfide compound to deposit white precipitates at ordinary temperature thawing, resulting in the cloudiness of the optical materials. The white precipitates are difficult to remove by ordinary filtration procedure because of severe clogging of filter. If a filter having a large pore diameter is used to prevent the clogging, the white precipitates are not completely removed. When the storage temperature exceeds 20° C., the episulfide compound is gradually yellowed, leading to the yellowing of the resultant optical materials.

The oxygen concentration of the storage atmosphere is preferably 21% by volume or lower to ensure the stable storage of the episulfide compound. When the oxygen concentration exceeds 21% by volume, the optical material is cloudy. Gases for use in attaining an oxygen concentration of 21% by volume or lower may include inert gases such as nitrogen, helium and argon, saturated hydrocarbon gases such as propane, sulfur-containing gases such as hydrogen sulfide and methyl mercaptan, and mixed gases having an oxygen concentration of 21% by volume or lower such as air. These gases may be used alone or in combination of two or more.

Further, the episulfide compound may be enhanced in storage stability by adding a stabilizer. In the present invention, it has been found that acid substances, preferably acidic organic substances, more preferably mercapto compounds and phenol compounds are effective as the stabilizer. Examples of the mercapto compounds include methyl mercaptan, ethyl mercaptan, n-propyl mercaptan, n-butyl mercaptan, allyl mercaptan, n-hexyl mercaptan, n-octyl mercaptan, n-decyl mercaptan, n-dodecyl mercaptan, n-tetradecyl mercaptan, n-hexadecyl mercaptan, n-octadecyl mercaptan, cyclohexyl mercaptan, isopropyl mercaptan, tert-butyl mercaptan, tert-nonyl mercaptan, tert-dodecyl mercaptan, benzyl mercaptan, 4-chlorobenzyl mercaptan, methyl thioglycolate, ethyl thioglycolate, n-butyl thioglycolate, n-octyl thioglycolate, methyl (3-mercaptopropionate), ethyl (3-mercaptopropionate), 3-methoxybutyl (3-methylpropionate), n-butyl (3-mercaptopropionate), 2-ethylhexyl (3-mercaptopropionate), n-octyl (3-mercaptopropionate), methanedithiol, 1,2-dimercaptoethane, 1,2-dimercaptopropane, 2,2-dimercaptopropane, 1,3-dimercaptopropane, 1,2,3-trimercaptopropane, 1,4-dimercaptobutane, 1,6-dimercaptohexane, bis(2-mercaptoethyl)sulfide, 1,2-bis(2-mercaptoethylthio)ethane, 1,5-dimercapto-3-oxapentane, 1,8-dimercapto-3,6-dioxaoctane, 2,2-dimethylpropane-1,3-dithiol, 3,4-dimethoxybutane-1,2-dithiol, 2-mercaptomethyl-1,3-dimercaptopropane, 2-mercaptomethyl-1,4-dimercaptobutane, 2-(2-mercaptoethylthio)-1,3-dimercaptopropane, 1,2-bis(2-mercaptoethylthio)-3-mercaptopropane, 1,1,1-tris(mercaptomethyl)propane, tetrakis(mercaptomethyl)methane, ethylene glycol bis(2-mercaptoacetate), ethylene glycol bis(3-mercaptopropionate), 1,4-butanediol bis(2-mercaptoacetate), 1,4-butanediol bis(3-mercaptopropionate), trimethylolpropane tris(2-mercaptoacetate), trimethylolpropane tris(3-mercaptopropionate), pentaerythritol tetrakis(2-mercaptoacetate), pentaerythritol tetrakis(3-mercaptopropionate), 1,1-dimercaptocyclohexane, 1,4-dimercaptocyclohexane, 1,3-dimercaptocyclohexane, 1,2-dimercaptocyclohexane, 1,4-bis(mercaptomethyl)cyclohexane, 1,3-bis(mercaptomethyl)cyclohexane, 2,5-bis(mercaptomethyl)-1,4-dithiane, 2,5-bis(2-mercaptoethyl)-1,4-dithiane, 2,5-bis(mercaptomethyl)-1-thiane, 2,5-bis(2-mercaptoethyl)-1-thiane, 1,4-bis(mercaptomethyl)benzene, 1,3-bis(mercaptomethyl)benzene, bis(4-mercaptophenyl)sulfide, bis(4-mercaptophenyl)ether, 2,2-bis(4-mercaptophenyl)propane, bis(4-mercaptomethylphenyl)sulfide, bis(4-mercaptomethylphenyl)ether, 2,2-bis(4-mercaptomethylphenyl)propane, 2,5-dimercapto-1,3,4-thiadiazole, 3,4-thiophenedithiol, thiophenol, 4-tert-butylthiophenol, 2-methylthiophenol, 3-methylthiophenol, 4-methylthiophenol, 1,2-dimercaptobenzene, 1,3-dimercaptobenzene, 1,4-dimercaptobenzene, allyl mercaptan, 2-vinylbenzyl mercaptan, 3-vinylbenzyl mercaptan, 4-vinylbenzyl mercaptan, 2-vinylthiophenol, 3-vinylthiophenol and 4-vinylthiophenol. Examples of the phenol compounds include phenol, o-cresol, m-cresol, p-cresol, 2-vinylphenol, 3-vinylphenol, 4-vinylphenol, o-hydroxybenzaldehyde, m-hydroxybenzaldehyde, p-hydroxybenzaldehyde, 4-tert-butylphenol, catechol, tert-butylcatechol, 2,6-di-tert-butylcresol, 2,6-di-tert-butylethylphenol, resorcin, hydroquinone, fluoroglucin, pyrogallol, cresol, ethylphenol, butylphenol, nonylphenol, hydroxyphenylacetic acid, hydroxyphenylpropionic acid, hydroxyphenylacetamide, methyl hydroxyphenylacetate, hydroxyphenethyl alcohol, hydroxyphenethylamine, hydroxybenzaldehyde, phenylphenol, bisphenol A, 2,2'-methylene-bis(4-methyl-6-tert-butylphenol), bisphenol F, bisphenol S, bisphenol Z, α-naphthol, β-naphthol, aminophenol, chlorophenol, 2,4,6-trichlorophenol, 2-hydroxythiophenol, 3-hydroxythiophenol and 4-hydroxythiophenol. These mercapto compounds and phenol compounds may be used alone or in combination of two or more. The addition amount thereof is preferably 0.001 to 10.0% by weight and more preferably 0.01 to 5.0% by weight based on the weight of the episulfide compound. When the addition amount is less than 0.001% by weight, it is difficult to sufficiently enhance the storage stability. When more than 10.0% by weight, optical properties of the resultant optical material such as refractive index and Abbe number are significantly adversely affected.

The episulfide compound is preferably stored in a container made of a material resistant thereto. Examples of such materials include glass, ceramic, silicon, metals such as aluminum, titanium, tantalum and zinc, alloys such as stainless steel, polyolefins such as PTFE, PFA and polypropylene, polyesters such as polyethylene terephthalate, and polyamides such as nylons. The container may be surface-coated with any of these materials.

Also, the episulfide compound is preferably stored under light-shielding condition to enhance the storage stability.

Examples of the curing catalysts for use in producing the optical materials from the episulfide compounds include amines, quaternary ammonium salts, quaternary phosphonium salts, phosphines, mineral acids, Lewis acids, organic acids, silicic acids, and boron tetrafluoride. Specific examples are described in Japanese Patent Application Laid-Open No. 10-28481.

The optical material of the present invention may also be produced by curing the episulfide compound by the polymerization with any of a compound having one or more functional groups reactive with the epithio group in the episulfide compound, a compound having one or more homopolymerizable functional groups in addition to one or more such functional groups, a compound having one or more homopolymerizable functional groups, and a compound having one homopolymerizable functional group also reactive with the epithio group. Examples of these compounds are described in Japanese Patent Application Laid-Open No. 9-255781.

When using an unsaturated compound, the use of a radical polymerization initiator is preferable. The radical polymerization initiator is not limited as long as it produces radicals by heating or irradiation of ultraviolet ray or electron beams. Specific examples thereof are described in Japanese Patent Application Laid-Open No. 9-255781.

The practical properties of the optical materials can be further improved by adding a known additive such as antioxidant and ultraviolet light absorber in the production process thereof. Since the optical materials of the present invention tend to be separated from a mold during the polymerization, the use or addition of a known external and/or internal adhesion modifier may be useful to improve the adhesion between the mold and the cured material.

To impart a good anti-oxidation property to the cured material, an anti-oxidizing component composed of a compound having one or more SH groups may be used alone or in combination with a known antioxidant. Examples of the compounds having one or more SH groups include mercaptans and thiophenols, each optionally having a unsaturated group such as vinyl, aromatic vinyl, methacrylic, acrylic and allyl groups. Specific examples thereof are described in Japanese Patent Application Laid-Open No. 9-255781.

To improve the dyeing ability, strength, etc., a compound having one or more active hydrogen atoms other than that of the SH group may be added. The active hydrogen atoms referred to herein are hydrogen atoms of hydroxyl, carboxyl or amide groups, or hydrogen atoms at 2-position of 1,3-diketones, 1,3-dicarboxylic acids and esters thereof or 3-ketocarboxylic acid and esters thereof. Examples of the compound having one or more such active hydrogen atoms include alcohols, phenols, mercaptoalcohols, hydroxythiophenols, carboxylic acids, mercaptocarboxylic acids, hydroxycarboxylic acids, amides, 1,3-diketones, 1,3-dicarboxylic acids and esters thereof, and 3-ketocarboxylic acids and ester thereof. These compounds may have an unsaturated group such as vinyl, aromatic vinyl, methacrylic, acrylic and allyl groups. Specific examples thereof are described in Japanese Patent Application Laid-Open No. 9-255781.

In the production of the cured resin optical materials of the present invention, the starting episulfide compound solely or a composition containing the episulfide compound is mixed with the catalyst and optionally with the additive such as the compound having two or more functional groups reactive with the epithio group in the episulfide compound, the compound having one or more homopolymerizable functional groups in addition to one or more functional groups reactive with the epithio group, the compound having one or more homopolymerizable functional groups, the compound having one homopolymerizable functional group also reactive with the epithio group, the anti-oxidizing component, the property modifier for the dyeability and strength, the adhesion modifier, the antioxidant other than the anti-oxidizing component, the ultraviolet light absorber, the radical polymerization initiator and various other modifiers in a total amount of 0.001 to 80% by weight, preferably 0.01 to 50% by weight, and more preferably 0.01 to 30% by weight based on the weight of the entire composition. The resultant mixture is cured by polymerization by the following method. The resultant mixture is cast into a mold made of glass or metals, cured by polymerization under heating, and then released from the mold to obtain the optical materials.

The episulfide compound alone or a composition containing it may be partly or completely pre-polymerized at −100 to 160° C. for 0.1 to 72 h in the presence or absence of the catalyst with or without stirring, added with the additive, etc., and then cast into a mold. The pre-polymerization is preferably carried out at −10 to 100° C. for 1 to 48 h, and more preferably at 0 to 60° C. for 1 to 48 h.

The curing time may be selected from the range of 0.1 to 100 h, and is usually 1 to 48 h. The curing temperature may be selected from the range of −10 to 160° C., and is usually −10 to 140° C. The polymerization can be conducted by suitably combining a step of holding the temperature at a specific polymerization temperature for a specific period of time, a step of increasing the temperature at a rate of 0.1 to 100° C./h and a step of decreasing the temperature at a rate of 0.1 to 100° C./h. To remove strains, as-cured optical material is preferably annealed at 50 to 150° C. for about 10 min to 5 h. Where necessary, the obtained optical material may be subjected to surface treatments for dyeing, hard coat formation, reflection prevention and clouding prevention.

The process for production of the cured resin optical material of the present invention is described in more detail below. As described above, the main starting materials and the secondary starting materials are mixed together, cast into a mold and cured therein. The episulfide compound alone or a composition containing the episulfide compound, the catalyst, the optional compounds such as the compound having two or more functional groups reactive with the epithio group in the episulfide compound, the compound having one or more functional groups reactive with the epithio group and one or more homopolymerizable functional groups, the compound having one or more homopolymerizable groups, and the compound having one homopolymerizable functional group also reactive with the epithio group, and optional additives such as the anti-oxidizing component, the property modifiers for dyeability and strength, the adhesion modifier, the stabilizers and radical polymerization initiators may be mixed together in the same vessel at the same time under stirring. Alternatively, the above materials may be mixed successively. The materials divided into two or more parts may be separately mixed and then further mixed together in the same vessel. The main starting materials, the optional compounds and the additives may be mixed in any order. In general, the mixing temperature and the mixing time are not limited as long as the components can be sufficiently mixed together. However, the use of an excessively high temperature and an excessively long time should be avoided because undesirable reactions take place between the materials and additives to increase viscosity and the operation of casting becomes difficult. Therefore, the mixing temperature is about −50 to 100° C., preferably −30 to 50° C. and more preferably −5 to 30° C. The mixing time is 1 min to 5 h, preferably 5 min to 2 h, more preferably 5 to 30 min and most preferably about 5 to 15 min. The materials and the additives are preferably subjected to degassing under vacuum before, during or after mixing to prevent formation of bubbles during casting and curing by polymerization. The vacuum degree of the degassing is about 10 Pa to 100 kPa and preferably 1,000 Pa to 40 kPa. To obtain a better quality of the optical material of the present invention, it is preferred to remove impurities by filtering these mixtures or the main and optional starting materials before mixing through a filter having a pore diameter of about 0.05 to 3 μm.

The present invention will be described in more detail by reference to the following examples, but it should noted that these examples are not intended to limit the scope of the present invention thereto. The episulfide compound and polymers obtained therefrom were evaluated by the following methods.

1. Turbidity of Liquid

A liquid was observed for turbidity level under irradiation of fluorescent light in dark room.
   None: No turbidity was found
   Found: Occurrence of turbidity was found

2. APHA

Measured according to JIS K0071.

3. Yellowness

A lens was measured for δYI value by a calorimeter. A lower δYI value indicates lower yellowness. In general, optical materials having a δYI value of 1.5 or lower are applicable to eyeglasses or spectacles.

4. Cloudiness

A lens was observed for cloudiness under irradiation of fluorescent light in dark room.
   None: Not cloudy
   Found: cloudy

PRODUCTION EXAMPLE 1

Into a flask equipped with a stirrer, a thermometer and a nitrogen inlet tube, were charged 365.0 g of bis(β-epoxypropyl)sulfide, 761.2 g of thiourea, 43.8 g of acetic anhydride and a solvent composed of 1.7 L of toluene and 3.4 L of methanol, and then, the reaction was allowed to proceed under nitrogen atmosphere at 20° C. for 10 h. After completion of the reaction, the reaction product was extracted with 4.3 L of toluene, washed with 520 mL of a 10% aqueous sulfuric acid and four 520-mL portions of water, followed by evaporating off the excessive solvent. After allowing to stand at −15° C. for one hour, 335.1 g of bis(β-epithiopropyl)sulfide was obtained by filtering through a PTFE filter having a pore diameter of 0.5 μm.

REFERENCE EXAMPLE 1

Bis(β-epithiopropyl)sulfide (100 parts by weight) prepared in Production Example 1 was immediately mixed with 0.1 part by weight of triethylamine as catalyst at room temperature under stirring to prepare a homogeneous liquid, which was then degassed, passed through a PTFE filter having a pore diameter of 1.0 μm, cast into a mold for flat lens having a thickness of 2.5 mm, and cured by polymerization in an oven while raising the temperature from 20° C. to 90° C. over 20 h, thereby preparing a lens. The obtained lens showed excellent heat resistance and physical properties. The lens not only had excellent optical properties, i.e., a refractive index of 1.71 and an Abbe number of 36, but also showed an excellent surface condition with little striae and surface deformation. The turbidity and APHA of the liquid immediately after preparation as well as the yellowness and cloudiness of the lens are shown in Table 1.

EXAMPLE 1

Bis(β-epithiopropyl)sulfide obtained in Production Example 1 was stored at 10° C. for 60 days in an atmosphere having an oxygen concentration of 21% by volume. After the storage, 100 parts by weight of bis(β-epithiopropyl)sulfide and 0.1 part by weight of triethylamine as catalyst were mixed at room temperature under stirring to obtain a homogeneous liquid, which was then degassed, passed through a PTFE filter having a pore diameter of 1.0 μm, cast into a mold for a flat lens having a thickness of 2.5 mm, and cured by polymerization in an oven while raising the temperature from 20° C. to 90° C. over 20 h, thereby preparing a lens. The obtained lens showed excellent heat resistance and physical properties. Like Reference Example 1, the lens not only had excellent optical properties, i.e., a refractive index of 1.71 and an Abbe number of 36, but also showed an excellent surface condition with little striae or surface deformation. The turbidity and APHA of the liquid after storage as well as the yellowness and cloudiness of the lens are shown in Table 1.

EXAMPLES 2-9

In accordance with the method of Production Example 1, each episulfide compound shown in Table 1 was produced, which was then stored in the same manner as in Example 1 except for employing the conditions shown in Table 1. The turbidity and APHA of the liquid after storage as well as the yellowness and cloudiness of the lens are shown in Table 1.

COMPARATIVE EXAMPLE 1

Bis(β-epithiopropyl)sulfide obtained in Production Example 1 was stored at −25° C. for one day in an atmosphere having an oxygen concentration of 21% by volume. After storage, bis(β-epithiopropyl)sulfide became a sherbet form, which turned cloudy when returned to ordinary temperature. Then, 100 parts by weight of bis(β-epithiopropyl)sulfide and 0.1 part by weight of triethylamine as catalyst were mixed at room temperature under stirring to obtain a homogeneous liquid, which was then degassed and attempted to filter through a PTFE filter having a pore diameter of 1.0 μm. However, the filter clogged, and no filtrate was obtained.

COMPARATIVE EXAMPLES 2-4

In accordance with the method of Production Example 1, each episulfide compound shown in Table 1 was produced, which was then stored in the same manner as in Example 1 except for employing the conditions shown in Table 1. The turbidity and APHA of the liquid after storage as well as the yellowness and cloudiness of the lens are shown in Table 1.

TABLE 1

| | | | Storage conditions | | |
|---|---|---|---|---|---|
| | Episulfide compound | Temperature (° C.) | Oxygen concentration (vol. %) | Gases other than oxygen | Stabilizer (ppm) |
| Reference Example | | | | | |
| 1 | BEPS | — | — | — | — |
| Examples | | | | | |
| 1 | BEPS | 10 | 21 | nitrogen | none |
| 2 | BEPS | −10 | 0 | nitrogen | none |
| 3 | BEPS | −10 | 21 | nitrogen | none |
| 4 | BEPE | 20 | 21 | nitrogen | none |
| 5 | BEPE | 20 | 0 | argon | none |
| 6 | BEPE | 20 | 21 | nitrogen | ME (1000) |
| 7 | BEPOE | 0 | 21 | nitrogen | none |
| 8 | BEPOE | 0 | 21 | nitrogen | PH (1000) |
| 9 | BEPOE | 0 | 50 | argon | none |
| Comparative Examples | | | | | |
| 1 | BEPS | −25 | 21 | nitrogen | none |
| 2 | BEPS | 30 | 21 | nitrogen | none |
| 3 | BEPOE | 30 | 50 | argon | none |
| 4 | BEPOE | 30 | 21 | nitrogen | PH (1000) |

Note:
BEPE: bis(β-epithiopropyl) ether; solidifying point: −30° C. or lower
BEPS: bis(β-epithiopropyl) sulfide; solidifying point: about −20° C.
BEPOE: bis(β-epithiopropyloxy)ethane; solidifying point: about −10° C.
ME: 2-mercaptoethanol
PH: phenol

| Storage time (day) | Evaluation of compound | | Evaluation of lens | |
|---|---|---|---|---|
| | Turbidity of liquid | APHA | Yellowness | Cloudiness |
| Reference Example | | | | |
| 1   0 | none | 10 | 0.6 | none |
| Examples | | | | |
| 1   60 | none | 15 | 0.8 | none |
| 2   60 | none | 10 | 0.6 | none |
| 3   60 | none | 15 | 0.7 | none |
| 4   60 | none | 20 | 0.8 | none |
| 5   80 | none | 15 | 0.7 | none |
| 6   60 | none | 10 | 0.6 | none |
| 7   80 | none | 15 | 0.7 | none |
| 8   80 | none | 10 | 0.6 | none |
| 9   80 | none | 20 | 0.9 | none |
| Comparative Examples | | | | |
| 1   1 | found | not measurable | no lens was obtained | |
| 2   60 | none | 50 | 1.8 | none |
| 3   60 | found | 80 | 3.0 | found |
| 4   60 | none | 40 | 1.8 | none |

INDUSTRIAL APPLICABILITY

The method of the present invention, wherein the episulfide compound having one or more epithio structural units represented by the formula (1) in one molecule is stored at a temperature ranging from its solidifying point to 20° C., enhances the storage stability and enables the long term storage. As a result, the episulfide compound is usable for stably producing a high quality optical material. Further, by reducing the oxygen concentration of the storage atmosphere to 21% by volume or lower or by previously adding an acidic substance such as mercapto compounds and phenol compounds, the episulfide compound can be stored more stably for a prolong period of time.

What is claimed is:

1. A method for storing an episulfide compound having in its molecule one or more epithio structural units represented by the formula (1):

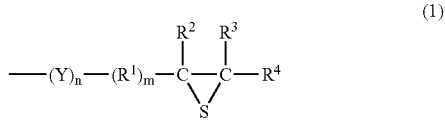

(1)

wherein $R^1$ is $C_1$-$C_{10}$ hydrocarbon group; $R^2$, $R^3$ and $R^4$ are each $C_1$-$C_{10}$ hydrocarbon group or hydrogen; Y is O, S, Se or Te; n is 0 or 1; and m is 0 or 1, said method comprising the steps of:
(a) filtering the episulfide compound at a temperature ranging from its solidifying point to 20° C. using a filter having a pore diameter of 0.05 to 10 μm; and subsequently,
(b) storing the episulfide compound at a temperature ranging from its solidification point to 10° C., under light-shielding conditions for at least 60 days while APHA is kept at 20 or lower.

2. The method according to claim 1, wherein the episulfide compound is stored at a temperature ranging from its solidification point to 10° C., after addition of an acidic substance.

3. The method according to claim 2, wherein the episulfide compound is stored in an atmosphere having an oxygen concentration of 21% by volume or lower.

4. The method according to claim 2, wherein the acidic substance is a mercapto compound or a phenol compound.

5. The method according to claim 2, wherein the episulfide compound is represented by the formula (2):

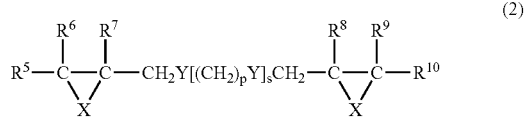

(2)

wherein $R^5$ to $R^{10}$ are each $C_1$-$C_{10}$ hydrocarbon group or hydrogen; X is S or O, the number of S being 50% or higher of a total number of S and O constituting three-membered rings; Y is O, S, Se or Te; p is an integer of 0 to 6; and s is an integer of 0 to 4.

6. The method according to claim 1, wherein the episulfide compound is stored in an atmosphere having an oxygen concentration of 21% by volume or lower.

7. The method according to claim 1, wherein the episulfide compound is represented by the formula (2):

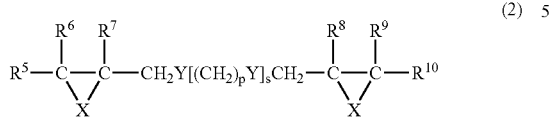
(2)

wherein $R^5$ to $R^{10}$ are each $C_1$-$C_{10}$ hydrocarbon group or hydrogen; X is S or O, the number of S being 50% or higher of a total number of S and O constituting three-membered rings; Y is O, S, Se or Te; p is an integer of 0 to 6; and s is an integer of 0 to 4.

8. The method according to claim 4, wherein the mercapto compound or phenol compound is added in an amount of 0.001 to 10.0% by weight based on the weight of the episulfide compound.

9. The method according to claim 8, wherein said amount is 0.01 to 5.0% by weight based on the weight of the episulfide compound.

10. A method for storing an episulfide compound having in its molecule one or more epithio structural units represented by the formula (1):

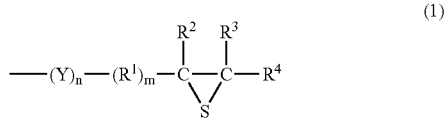
(1)

wherein $R^1$ is $C_1$-$C_{10}$ hydrocarbon group; $R^2$, $R^3$ and $R^4$ are each $C_1$-$C_{10}$ hydrocarbon group or hydrogen; Y is O, S, Se or Te; n is 0 or 1 and m is 0 or 1,
said method comprising the steps of:
(a) filtering the episulfide compound at a temperature ranging from its solidifying point to 20° C. using a filter having a pore diameter of 0.05 to 10 μm; and subsequently,
(b) storing the episulfide compound at a temperature ranging from its solidification point to 10° C., under light-shielding conditions for 60 days or more while the APHA is kept at 20 or lower, after addition of an acidic substance in an amount of 0.001 to 10.0% by weight based on the weight of the episulfide compound, and in an atmosphere having an oxygen concentration of 21% by volume or lower.

11. The method according to claim 10, wherein the acidic substance is a mercapto compound or a phenol compound.

12. The method according to claim 10, wherein the episulfide compound is represented by the formula (2):

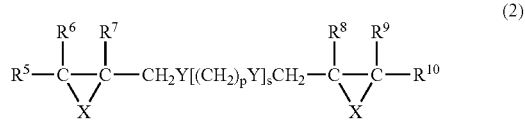
(2)

wherein $R^5$ to $R^{10}$ are each $C_1$-$C_{10}$ hydrocarbon group or hydrogen; X is S or O, the number of S being 50% or higher of a total number of S and O constituting three numbered rings; Y is O, S, Se or Te; p is an integer of 0 to 6; and s is an integer of 0 to 4.

13. The method according to claim 11, wherein the mercapto compound or a phenol compound is added in an amount of 0.01 to 5.0% by weight based on the weight of the episulfide compound.

14. The method according to claim 1, wherein the atmosphere in which the episulfide compound is stored contains argon.

15. The method according to claim 10, wherein the atmosphere in which the episulfide compound is stored contains argon.

* * * * *